United States Patent
Sharko et al.

(10) Patent No.: US 9,587,188 B2
(45) Date of Patent: Mar. 7, 2017

(54) PROCESS FOR PREPARING A BRANCHED ESTER AND USE THEREOF

(71) Applicant: SHELL OIL COMPANY, Houston, TX (US)

(72) Inventors: Paul Theodore Sharko, Houston, TX (US); James Grace Crump, Houston, TX (US); Naga Roobini Aruleswaran, Kajang Selangor D.E. (MY)

(73) Assignee: SHELL OIL COMPANY, Houston, TX (US)

(*) Notice: Subject to any disclaimer, the term of this patent is extended or adjusted under 35 U.S.C. 154(b) by 84 days.

(21) Appl. No.: 14/569,887

(22) Filed: Dec. 15, 2014

(65) Prior Publication Data
US 2015/0166912 A1   Jun. 18, 2015

Related U.S. Application Data

(60) Provisional application No. 61/916,949, filed on Dec. 17, 2013.

(51) Int. Cl.
| | | |
|---|---|---|
| *C10L 1/19* | (2006.01) | |
| *C10L 10/16* | (2006.01) | |
| *C07C 67/08* | (2006.01) | |

(52) U.S. Cl.
CPC .............. *C10L 1/19* (2013.01); *C07C 67/08* (2013.01); *C10L 10/16* (2013.01); *C10L 2200/04* (2013.01); *C10L 2270/026* (2013.01)

(58) Field of Classification Search
USPC .................................................. 44/388–402
See application file for complete search history.

(56) References Cited

U.S. PATENT DOCUMENTS

| | | | | |
|---|---|---|---|---|
| 3,420,875 | A | | 1/1969 | DiSalvo et al. |
| 3,428,654 | A | | 2/1969 | Rubinfeld et al. |
| 3,462,525 | A | | 8/1969 | Levinsky et al. |
| 3,506,580 | A | | 4/1970 | Rubinfeld et al. |
| 3,524,864 | A | | 8/1970 | Rubinfeld |
| 3,579,537 | A | | 5/1971 | Rubinfeld et al. |
| 4,491,526 | A | | 1/1985 | Deck |
| 5,100,697 | A | | 3/1992 | Nielsen |
| 5,389,113 | A | * | 2/1995 | Demmering ............ C10L 1/026 44/388 |
| 5,849,960 | A | | 12/1998 | Singleton et al. |
| 6,017,369 | A | * | 1/2000 | Ahmed .................... C10L 1/026 44/302 |
| 6,242,406 | B1 | | 6/2001 | Katsuda et al. |
| 7,166,739 | B2 | * | 1/2007 | Walele .................... A61K 8/37 424/63 |
| 7,462,730 | B2 | * | 12/2008 | Raney ..................... A61K 8/37 424/401 |
| 7,696,136 | B2 | * | 4/2010 | Migdal .................... C10L 1/19 44/388 |
| 7,888,307 | B2 | | 2/2011 | Singleton et al. |
| 7,931,703 | B2 | * | 4/2011 | Roby ...................... C10L 1/026 44/307 |
| 8,057,558 | B2 | * | 11/2011 | Zhou ....................... C10L 1/026 44/308 |
| 8,664,166 | B2 | * | 3/2014 | Raney .................... C09K 8/584 507/252 |
| 8,664,167 | B2 | * | 3/2014 | Raney .................... C09K 8/584 507/252 |
| 2003/0166495 | A1 | | 9/2003 | Wang et al. |
| 2005/0192200 | A1 | | 9/2005 | Hecht et al. |
| 2006/0183659 | A1 | | 8/2006 | Dovey et al. |
| 2008/0146482 | A1 | | 6/2008 | Schneiderman et al. |
| 2008/0171672 | A1 | | 7/2008 | Cano et al. |
| 2008/0226808 | A1 | | 9/2008 | Meli et al. |
| 2008/0249336 | A1 | | 10/2008 | Singleton et al. |
| 2011/0028374 | A1 | | 2/2011 | Fossum et al. |
| 2011/0162263 | A1 | * | 7/2011 | Vilardo ................... C10L 10/14 44/389 |
| 2014/0026331 | A1 | | 1/2014 | Frankenbach et al. |

OTHER PUBLICATIONS

Sern, C. H., et al.; "Synthesis of Palmitic Acid-Based Ester and their Effect on the Pour Point of Palm Oil Methyl Esters"; Journal of Oil Palm Research, pp. 542-547; 2008.

Dailey, O.., et al. "Synthesis and Characterization of Branched-Chain Derivative of Methyl Oleate"; CLEAN—Soil Air Water; pp. 687-693; 2008.

* cited by examiner

*Primary Examiner* — Ellen McAvoy

(57) ABSTRACT

The present invention provides a process for preparing a branched ester, comprising reacting a branched primary alcohol composition, having from 8 to 28 carbon atoms and an average number of branches per molecule of from 0.7 to 3.0, said branching comprising methyl and ethyl branches, with an acid.

In another aspect, the invention provides a process for preparing a branched ester, pour point depressants for use in fuels, and the use of a branched primary alcohol composition.

9 Claims, No Drawings

PROCESS FOR PREPARING A BRANCHED ESTER AND USE THEREOF

The present application claims the benefit of pending U.S. Provisional Patent Application Ser. No. 61/916949, filed Dec. 17, 2013, the entire disclosure of which is hereby incorporated by reference.

FIELD OF THE INVENTION

The invention pertains to a process for preparing a branched ester and the use thereof.

BACKGROUND OF THE INVENTION

Long chain alcohols having about 8 to 28 carbon atoms and their derivatives have considerable commercial importance in a variety of applications. These include consumer products such as detergents, soaps, personal care products, drug products, as well as industrial products such as surfactants, degreasers, industrial cleaners, agricultural adjuvants, textile processing chemicals, waxes, mining chemicals, oilfield chemicals, metal working fluids and additives for lubricating oils and greases.

There are several commercial routes employed for obtaining alcohol molecules of this size:
1. Naturally occurring fats and oils of either animal or vegetable origin can be cracked and refined to yield predominantly straight chain alcohols with even carbon numbers.
2. Ethylene can be oligomerized by the Ziegler process yielding straight chain alcohols with even carbon numbers.
3. Linear olefins can be hydroformylated to alcohols of both odd and even carbon numbers. Hydroformylation introduces branching, primarily at the 2-carbon site. Depending on the catalyst used and the process conditions employed the degree of branching can be controlled from as low as 18% to 50% or more.
4. Short chain olefins, (e.g. C3 or C4) can be oligomerized to yield branched olefins with 2 or more branches per molecule. These branched olefins can then be hydroformylated to yield highly branched alcohols.

These alcohols are also characterized by the presence of quaternary carbon atoms within their molecular backbones.

These alcohols are produced by any one of commercial processes, such as the oxo or hydroformylation of long chain olefins. Typical long chain alcohols are the commercially available NEODOL® alcohols made by Shell Chemical Company, the EXXAL® alcohols available from Exxon Chemical, and the LIAL® alcohols available from Sasol.

However, there remains a need for suitable alcohol and alcohol derivatives for particular applications

SUMMARY OF THE INVENTION

It has now been found that an existing alcohol, previously introduced for the production of surfactants for laundry washing, confers other benefits that were not previously anticipated. These benefits stem from the bulk physical properties of these alcohols and their derivatives. One particular use is the use of the alcohol to make a branched ester, which can be used as a pour point depressant in fuel, in particular diesel fuel Accordingly, the present invention therefore provides a process for preparing a branched ester, comprising reacting a branched primary alcohol composition, having from 8 to 28 carbon atoms and an average number of branches per molecule of from 0.7 to 3.0, said branching comprising methyl and ethyl branches, with an acid.

In another aspect, the invention provides a process for preparing a branched ester, comprising oxidizing a branched primary alcohol composition, having from 8 to 28 carbon atoms and an average number of branches per molecule of from 0.7 to 3.0, said branching comprising methyl and ethyl branches, to convert at least part of the alcohol in the branched primary alcohol composition to a branched primary alcohol composition-derived acid; and reacting the acid with a second alcohol.

In another aspect, the invention provides a pour point depressant for use in fuels, wherein the pour point depressant is an ester prepared by a process according to first aspect of the invention.

In yet another aspect, the invention provides a pour point depressant for use in fuels, wherein the pour point depressant is an ester prepared by a process according to second aspect of the invention In still another aspect, the invention provides the use of a branched primary alcohol composition, having from 8 to 28 carbon atoms and an average number of branches per molecule of from 0.7 to 3.0, said branching comprising methyl and ethyl branches, to prepare branched esters for use as pour point depressants in fuels.

DETAILED DESCRIPTION OF THE INVENTION

U.S. Pat. No. 5,849,960 discloses a process for producing long chain alcohols starting with C7 to C35 mono-olefins. The isomerized alcohols of U.S. Pat. No. 5,849,960 are typically referred to as branched primary alcohol compositions (hereinafter also BPAC).

A skeletal isomerization process is performed on the olefins producing branched mono-olefins with at least 0.7 branches per molecule. These branched olefins are then hydroformylated to produce alcohols with at least 0.7 branches per molecule, but with fewer than 0.5% of quaternary carbon atoms. These properties distinguish these alcohols from alcohols previously in commerce.

One example of a BPAC as described in U.S. Pat. No. 5,849,960 is NEODOL® 67, a mixture primarily of C16 and C17 alcohols and with an average branching of about 1.5 branches per molecule. This particular combination of alcohol chain length and branching was found to be particularly useful for the production of surfactants for laundry washing. The sulfated derivative of this alcohol is long enough to effectively roll up and remove soils from fabrics. The branching in this molecule is sufficient to prevent the close range ordering that would cause the sulfate derivative to precipitate out of solution at the low temperatures commonly found in typical laundry wash cycles. The low degree of quaternary carbon atoms ensures ready biodegradability that is needed for laundry detergent surfactants.

It has now surprisingly been discovered that the degree of branching in this molecule confers other benefits that were not anticipated. Without wishing to be bound to any particular embodiment it is believed that these benefits stem from the bulk physical properties of these alcohols and their derivatives. One example is evident as the alcohols are cooled to the solidification point. BPACs will remain liquid to lower temperatures than their unbranched or less highly branched analogs. For example NEODOL® 67 is a liquid at room temperature, while C16 and C17 linear alcohols are both solids.

Another benefit afforded by BPACs is their chemical stability. In contrast to unsaturated long-chain alcohols that are derived from naturally occurring fats and oils, the alcohols in the BPACs are almost fully saturated (Iodine number<0.5). As a result, they demonstrate a high degree of oxidative stability at high temperature, a resistance to reactions involving, for example, sulfur-containing, nitrogen-containing, or halogen-containing chemical moieties, as well as resistance to molecular breakdown due to hydrolysis at high or low pH.

The disorder introduced into the hydrocarbon backbone of these branched long chain alcohols, as well as the high degree of saturation, results in important properties of both the alcohol and derivatives of the alcohol.

In recognition of the before unknown beneficial properties of these BPACs and their derivatives, the present invention provides the novel and inventive uses of the BPAC and derivatives of the BPAC, wherein the BPAC and derivatives of the BPAC are defined in more detail herein below.

A first embodiment of the invention provides a process for preparing a branched ester, comprising reacting a BPAC, having from 8 to 28 carbon atoms and an average number of branches per molecule of from 0.7 to 3.0, said branching comprising methyl and ethyl branches, with an acid.

Preferably, the acid is a short fatty chain acid. Short chain fatty acids are a sub-group of fatty acids comprising an aliphatic group of two to six carbons. Preferably the short chain fatty acid is selected from the group consisting of formic acid, acetic acid, propionic acid, isobutyric acid (2-methylpropanoic acid), butyric acid, isovaleric acid (3-methylbutanoic acid) and valeric acid. The short chain fatty acids may be either linear or branched Alternatively, the branched ether is prepared by a process for preparing a branched ester, comprising oxidizing a BPAC, having from 8 to 28 carbon atoms and an average number of branches per molecule of from 0.7 to 3.0, said branching comprising methyl and ethyl branches, to convert at least part of the alcohol in the BPAC to an BPAC derived acid; and reacting the acid with a second alcohol.

Preferably, the second alcohol is an alcohol comprising 1 to 6 carbon atoms. The second alcohols may be either linear or branched.

The invention further provides the use of a BPAC, having from 8 to 28 carbon atoms and an average number of branches per molecule of from 0.7 to 3.0, said branching comprising methyl and ethyl branches, to prepare branched esters for use as pour point depressants in fuels.

In addition the invention provides a pour point depressant for use in fuels, in particular diesel fuel, wherein the pour point depressant is an ester prepared by reacting a BPAC, having from 8 to 28 carbon atoms and an average number of branches per molecule of from 0.7 to 3.0, said branching comprising methyl and ethyl branches, with an acid, preferably a short fatty chain acid. Short chain fatty acids are a sub-group of fatty acids comprising an aliphatic group of two to six carbons. Preferably the short chain fatty acid is selected from the group consisting of formic acid, acetic acid, propionic acid, isobutyric acid (2-methylpropanoic acid), butyric acid, isovaleric acid (3-methylbutanoic acid) and valeric acid. The short chain fatty acids may be either linear or branched Alternatively, the invention provides a pour point depressant for use in fuels, in particular diesel fuel, wherein the pour point depressant is an ester prepared by:

oxidizing a BPAC, having from 8 to 28 carbon atoms and an average number of branches per molecule of from 0.7 to 3.0, said branching comprising methyl and ethyl branches, to convert at least part of the alcohol in the branched primary alcohol composition to a branched primary alcohol composition-derived acid; and reacting the acid with a second alcohol, preferably a second alcohol comprising 1 to 6 carbon atoms. The second alcohols may be either linear or branched.

The long chain highly branched hydrocarbon chain of either the alcohol of the BPAC or the BPAC derived acid assures good solubility in a fuel or lubricant base. The ester group provides the disorder required to effect the pour point depression benefit.

One of the major problems associated with biodiesel is its poor properties under low temperatures, indicated by relatively high pour point. (Sern, C. H., May, C. Y., Zakaria, Z., & Daik, R. (2008). Synthesis of Palmitic Acid-Based Ester and their Effect on the Pour Point of Palm Oil Methyl Esters. Journal of Oil Palm Research, 542-547.) The problem is particularly severe in palm methyl ester based biodiesel due to its high proportion of saturated, linear hydrocarbon chains. The crystallization temperature of methyl esters can be reduced by introducing branching into the hydrocarbon backbone of the ester. (Dailey, O., Prevost, N., & Strahan, G. (2008). Synthesis and Characterization of Branched-Chain Derivative of Methyl Oleate. CLEAN—Soil Air Water, 687-693.) The pour point depressants based on the branched esters of the present invention may be suitable as additives to biodiesel for low-temperature service.

Isomerized alcohol derivatives may also be used effectively as pour-point depressants in fuel additives for passenger car motor fuels (gasoline). Pour-point depressants using isomerized alcohol derivatives are effective as well in oil additives for both commercial trucks and off-road equipment, in heavy-duty motor oil (HDMO) and in oil additives for passenger car motor oil (PCMO).

A second embodiment of the invention provides a concentrated detergent composition comprising an anionic surfactant composition containing at least one sulfate, sulfonate, carboxylate, or phosphate of a BPAC, having from 8 to 28 carbon atoms and an average number of branches per molecule of from 0.7 to 3.0, said branching comprising methyl and ethyl branches, or at least one sulfate, sulfonate, carboxylate, or phosphate of an alkoxylated derivative of such BPAC, wherein the concentrated detergent comprises more than 40 wt % of solid matter based on the weight of the concentrated detergent composition.

Preferably, the concentrated detergent composition comprises more than 50 wt %, more preferably more than 60 wt % of solid matter based on the weight of the concentrated detergent composition.

Preferably, the concentrated detergent composition also comprises water. Optionally, the concentrated detergent composition further comprises additives that improve either the stability of the concentrated detergent composition or the functionality of the concentrated detergent composition.

Preferably, the anionic surfactant composition of the concentrated detergent composition contains at least one alcohol sulphate.

Preferably, the anionic surfactant composition of the concentrated detergent composition contains at least one alkoxy alcohol sulphate, more preferably the alkoxy alcohol sulphate is an ethoxy alcohol sulfate.

In another aspect, the invention provides a process for preparing the concentrated detergent composition according to the invention, comprising reacting the BPAC, having from 8 to 28 carbon atoms and an average number of branches per molecule of from 0.7 to 3.0, said branching comprising methyl and ethyl branches, or alkoxylated derivative of such BPAC with an acidic moiety and then neutralized converting it to the salt of an anionic surfactant.

Preferably, the acidic moiety is a sulphur containing acidic moiety, preferably $SO_3$.

The processes for preparing the concentrated detergent composition according to the invention may include, first preparing a diluted detergent and subsequently concentrating the diluted detergent composition to obtain the detergent composition according to the invention.

In a further aspect, the invention provides the use of a BPAC, having from 8 to 28 carbon atoms and an average number of branches per molecule of from 0.7 to 3.0, said branching comprising methyl and ethyl branches, an alkoxylated derivative of such BPAC to prepare a concentrated detergent composition.

The BPAC and alkoxylated derivatives of such BPAC are suitable raw materials the production of for anionic surfactants. The alcohol or alkoxylated alcohol is preferably reacted with an acidic moiety and then neutralized converting it to the salt of an anionic surfactant. Such surfactants are preferably made by converting the BPAC and alkoxylated derivatives thereof to a sulfate, sulfonate, carboxylate, phosphate, or derivatives with a similar head group. It is known that these anionic surfactants form gel-like liquid crystal phases at moderate surfactant concentrations. These liquid crystal phases are slow to hydrate and difficult to handle due to their high viscosity. Use of an isomerized hydrocarbon chain rather than a less-highly branched chain, such as present in the BPAC and alkoxylated derivatives thereof, introduces disorder into liquid crystal phases, reducing their viscosity and maintaining a free flowing state to significantly higher concentrations. These more highly concentrated fluids can be shipped more economically due to their lower water content. The solid matter herein refers to all residual BPAC and all compounds directly derived from the BPAC and alkoxylated derivatives thereof.

To demonstrate the advantage of using the BPAC and alkoxylated derivatives thereof for producing concentrated detergents, two alkyl sulfate surfactants were prepared. Each was synthesized from an alcohol composed primarily of C12 and C13 hydrocarbon chains. One sample was prepared with approximately 0.18 branches per molecule. The other was derived from a BPAC with approximately 1.5 branches per molecule. Both were prepared at about 26% solids and gradually concentrated. The alkyl sulfate with 0.18 branches per molecule began forming a solid precipitate at 30% solids. The alkyl sulfate prepared from the BPAC remained a free-flowing liquid without forming a precipitate even at 50% solids.

A third embodiment of the invention provides the use of a BPAC, having from 8 to 28 carbon atoms and an average number of branches per molecule of from 0.7 to 3.0, said branching comprising methyl and ethyl branches, to prepare wax esters.

The wax esters are preferably synthesized from a long chain fatty alcohol and a long chain fatty ester. Preferably the BPAC is used as the fatty alcohol. Alternatively, the BPAC, following an oxidation step, is preferably used as the fatty acid. In a more preferred embodiment a BPAC is used as the fatty alcohol and following an oxidation step, a BPAC is used as the fatty acid is used as the fatty acid. The primary BPAC used as the fatty alcohol may be the same or different from the BPAC used to prepare the fatty acid.

Use of an isomerized hydrocarbon chain rather than a less-highly branched chain has the advantage that it will result in a wax ester that may have a lower melting point, may be softer, may be easier to spread, and may be more lubricating. These properties could be highly beneficial to their inclusion in candle waxes, wax coatings, cosmetics, polishes for shoes, vehicles, furniture and food products, pharmaceutical products, confectionary products, or a variety of other applications in home care, personal care, pharmaceutical or industrial applications.

Therefore, the invention also provides for the use of a fatty ester prepared from at least a BPAC, having from 8 to 28 carbon atoms and an average number of branches per molecule of from 0.7 to 3.0, said branching comprising methyl and ethyl branches in candle waxes, wax coatings, cosmetics, polishes for shoes, vehicles, furniture and food products, pharmaceutical products, confectionary products, or a variety of other applications in home care, personal care, pharmaceutical or industrial applications.

The invention also provides candle waxes, wax coatings, cosmetics, polishes for shoes, vehicles, furniture and food products, pharmaceutical products, confectionary products comprising a fatty ester prepared from at least a BPAC, having from 8 to 28 carbon atoms and an average number of branches per molecule of from 0.7 to 3.0, said branching comprising methyl and ethyl branches.

In a particular embodiment the invention provides for the use of a BPAC, having from 8 to 28 carbon atoms and an average number of branches per molecule of from 0.7 to 3.0, said branching comprising methyl and ethyl branches, to prepare wax esters for use in mold release aids.

U.S. Pat. No. 5,100,697 teaches the use of low-melting wax esters in the formulation of concrete mold release aids. Wax esters melting below 35° C. and preferred in this application and those with a melting point below 25° C. are particularly preferred. The use of isomerized hydrocarbon backbones in either the acid or the alcohol moiety would enable the formulator to select from a broader range of choices within the preferred melting range The invention therefore also provides a mold release aid comprising a fatty ester prepared from at least a BPAC, having from 8 to 28 carbon atoms and an average number of branches per molecule of from 0.7 to 3.0, said branching comprising methyl and ethyl branches.

A fourth embodiment of the invention the use of a BPAC, having from 8 to 28 carbon atoms and an average number of branches per molecule of from 0.7 to 3.0, said branching comprising methyl and ethyl branches, and alkoxylated derivatives of such BPAC to prepare metallic soaps.

In addition the invention provides for the use of metallic soaps, prepared from a BPAC, having from 8 to 28 carbon atoms and an average number of branches per molecule of from 0.7 to 3.0, said branching comprising methyl and ethyl branches, and alkoxylated derivatives of such BPAC, as detergent in lubricant compositions.

Reference is made to Rizvi, S. Q. (2009), A Comprehensive Review of Lubricant Chemistry, Technology, Selection, and Design, West Conshohocken PA: ASTM International, which is herein incorporated by reference. Rizvi describes the development of metallic soaps using naturally occurring fats and oils as a raw material. Rizvi describes the limitations encountered when using these soaps as detergents in lubricants. Straight chain hydrocarbon backbones produce soaps that are high melting and have low oil solubility/miscibility. Unsaturated hydrocarbon backbones provide the low temperature performance needed in lubricant detergents, but the unsaturation raises the degree of oxidation susceptibility as well. Rizvi points out that metallic soaps incorporating branched hydrocarbon backbones afford the low temperature performance of unsaturated soaps while retaining the low susceptibility to oxidation afforded by saturation. Rizvi mentions isostearate soaps as an example of branched soaps derived from naturally occurring fatty acids. Soaps can preferably be produced from BPACs by oxidizing them to acids and subsequent neutralization. Such soaps can be designed with a particular chain length and degree of branching that affords the formulator a broad degree of flexibility.

A fifth embodiment of the invention provides the use of a BPAC, having from 8 to 28 carbon atoms and an average number of branches per molecule of from 0.7 to 3.0, said branching comprising methyl and ethyl branches, and derivatives of such BPAC in metalworking fluids.

In addition the invention provides for a metalworking fluid, comprising a BPAC, having from 8 to 28 carbon atoms and an average number of branches per molecule of from 0.7 to 3.0, said branching comprising methyl and ethyl branches, and derivatives of such BPAC.

Metalworking fluids (MWFs) are used to reduce heat and friction and to remove metal particles in industrial machining and grinding operations. There are numerous formulations, ranging from straight oils (such as petroleum oils) to water-based emulsions. Fatty alcohols and their derivatives are used in several types of additives including emulsifiers, couplers, extreme pressure and lubricity agents, and corrosion inhibitors. (Rizvi, 2009) Metalworking additives have been synthesized with both linear and unsaturated hydrocarbon backbones. The replacement of these by isomerized hydrocarbon backbones takes advantage of their relatively low pour point and oxidative stability in demanding applications, including applications involving high-temperature process conditions. A preferred BPAC, having from 8 to 28 carbon atoms and an average number of branches per molecule of from 0.7 to 3.0, said branching comprising methyl and ethyl branches, and derivatives of such BPAC comprises an alkoxylated derivative of BPAC, having from 8 to 28 carbon atoms and an average number of branches per molecule of from 0.7 to 3.0, said branching comprising methyl and ethyl branches. Such alkoxylated branched primary alcohols compositions may be used as emulsifiers in high temperature cutting fluids.

The metalworking fluids preferably consist of a base oil blended with one or more of additives, including at least one compound selected from the group consisting of BPAC, having from 8 to 28 carbon atoms and an average number of branches per molecule of from 0.7 to 3.0, said branching comprising methyl and ethyl branches, and derivatives of such BPAC, chosen to enhance fluid performance in the application of choice.

Synthetic esters have been in recent years used in finished MWF formulations to overcome shortcomings of formulations comprising mineral oils. Synthetic esters are also regularly used in water-miscible fluids. Some key features of synthetic esters include low volatility, hydrolytic and oxidative stability. The polarity of esters give them an affinity for each other in the liquid state. This reduces their tendency to evaporate at a given temperature than a non-polar molecule such as a hydrocarbon mineral oil and therefore have lower volatility. In addition, the polarity of esters also attract them to metal surfaces where they form a molecular layer which not only lubricates but also protects the metal from oxidation and corrosion.

Four main classes of synthetic esters used are:
(1) Fatty acid esters—these are made from naturally derived fatty acids reacted with a synthetic alcohol because the natural fatty acid constituent typically is prone to oxidation and rancidity at elevated temperatures. The resulting synthetic fatty acid ester has superior oxidative and hydrolytic stability and can be designed to meet the viscosity and volatility profile and other characteristics required for the application.
(2) Diesters—made from synthetic diacids and synthetic alcohols. Whilst not based on renewable sources, diesters have two ester groups and are fully saturated so they are better than fatty acid esters at both high and low temperatures.
(3) Polyol esters—contain three or more ester groups and this increases viscosity and lowers volatility further. The polyol center is extremely stable at high temperature so polyol esters are preferred in hot operations where they give long life and resist varnish and deposit formation. The acid component can be renewable or fully synthetic. Synthetics optimize thermal stability and renewable acids are required if the oil must be readily biodegradable
(4) Complex polyol esters—polymeric hybrids of polyol esters and diacids which are combined to achieve high viscosities and a very high viscosity index, tack and boundary lubrication. These can be manufactured with a large percentage of renewable carbons and many types are readily biodegradable.

Based on the short description above and property requirements, there is opportunity for BPAC to be used as the synthetic alcohol moiety to be reacted with corresponding fatty acids. The properties of NEODOL®67 such as full saturation and absence of quaternary carbons could help in meeting oxidative and thermal stability requirements. The high branching content may not contribute to high viscosity, but where smaller synthetic alcohols are typically used, the branching could potentially provide a counter-balance against volatility. The high branching in turn may be beneficial for handling, miscibility and dispersion in the complex mixture with other compositions. The high biodegradability of the BPAC and its derivatives may be an essential feature in the synthesis of the esters, albeit from non-natural feedstock. Biodegradability of the ester oils is mainly depending on the characteristics of the base fluids and not affected by other additives. This is will be especially important in niche markets like making parts for medical purposes.

A sixth embodiment of the invention provides the use of a BPAC, having from 8 to 28 carbon atoms and an average number of branches per molecule of from 0.7 to 3.0, said branching comprising methyl and ethyl branches, and derivatives of such BPAC in the synthesis of methacrylate/acrylate esters.

The corresponding esters obtained from the BPAC may be used in various applications such as oil additives, viscosity index improver, pour point depressants, thickening agent, coatings, inks and resins. In addition, these esters can also form homopolymers and copolymers, when prepared with acrylic acid and its salts, amides and esters, and with methacrylates, acrylonitrile, maleic acid esters, vinyl acetate, vinyl chloride, vinylidene chloride, styrene, butadiene, unsaturated polyesters and drying oils, etc.

The key features of these esters include low volatility and hydrophobicity from the long hydrocarbon chain, which impart flexibility, low shrinkage, weatherability and impact strength. Another aspect that is an important feature is chemical resistance.

A particularly preferred use of the methacrylate/acrylate esters thus prepared is the use as oil additives, more in particular pour point depressants and viscosity index improvers.

The use of oleo-based C16 and C18 alcohols or a combination thereof to synthesize the methacrylate/acrylate esters has been reported. A key advantage of using NEODOL®67, or NEODOL® 25, a branched primary alcohol blend of C12, C13, C14 and C15 alcohols, compared to the use of oleo C16-18 alcohols may be the higher branching content, which will help to further reduce the pour point. In addition, the high saturation could impart the required chemical resistance and oxidative stability where oleo alcohol based esters may not be able to meet. With increasing environmental legislations on lubricants and performance e.g. longer drain interval, fuel economy, higher operating temperatures from smaller engines—the need for pour point depressants or viscosity index improvers that have high stability in larger operating windows will become increasingly important. Furthermore, NEODOL®67 based esters could offer better solubility in comparison to oleo C16-C18 alcohol based esters in base oils from Group II, III and IV.

A seventh embodiment of the invention provides the use of a BPAC, having from 8 to 28 carbon atoms and an average number of branches per molecule of from 0.7 to 3.0, said branching comprising methyl and ethyl branches, and derivatives of such BPAC as thickening agents in hydraulic fluids. Preferably, the BPAC, having from 8 to 28 carbon atoms and an average number of branches per molecule of from 0.7 to 3.0, said branching comprising methyl and ethyl branches, and derivatives of such BPAC is alkoxylated derivative of a BPAC, having from 8 to 28 carbon atoms and an average number of branches per molecule of from 0.7 to 3.0, said branching comprising methyl and ethyl branches.

The use of alcohol alkoxylates to thicken water-based hydraulic fluids is well known (e.g. U.S. Pat. No. 4,491,526). Alkoxylates produced from linear or lightly branched hydrophobes are prone to separate, forming gel-like structures at low temperature. Under these conditions the hydraulic fluid could lose its free-flowing characteristics, blocking channels and ports. The substitution of isomerized alcohols may extend the useful temperature range of these fluids to lower temperatures.

As used herein, the phrase average number of branches per molecule chain refers to the average number of branches per alcohol molecule, as measured by 13C Nuclear Magnetic Resonance (13C NMR) as discussed below. The average number of carbon atoms in the chain are determined by gas chromatography.

Various references will be made throughout this specification and the claims to the percentage of branching at a given carbon position, the percentage of branching based on types of branches, average number of branches, and percentage of quaternary atoms. These amounts are to be measured and determined by using a combination of the following three 13C-NMR techniques. (1) The first is the standard inverse gated technique using a 45-degree tip 13C pulse and 10 s recycle delay (an organic free radical relaxation agent is added to the solution of the branched alcohol in deuterated chloroform to ensure quantitative results). (2) The second is a J-Modulated Spin Echo NMR technique (JMSE) using a 1/J delay of 8 ms (J is the 125 Hz coupling constant between carbon and proton for these aliphatic alcohols). This sequence distinguishes carbons with an odd number of protons from those bearing an even number of protons, i.e. CH3/CH vs CH2/Cq (Cq refers to a quaternary carbon). (3) The third is the JMSE NMR "quat-only" technique using a 1/2 J delay of 4 ms which yields a spectrum that contains signals from quaternary carbons only. The JSME NMR quat only technique for detecting quaternary carbon atoms is sensitive enough to detect the presence of as little at 0.3 atom % of quaternary carbon atoms. As an optional further step, if one desires to confirm a conclusion reached from the results of a quat only JSME NMR spectrum, one may also run a DEPT-135 NMR sequence. We have found that the DEPT-135 NMR sequence is very helpful in differentiating true quaternary carbons from breakthrough protonated carbons. This is due to the fact that the DEPT-135 sequence produces the "opposite" spectrum to that of the JMSE "quat-only" experiment. Whereas the latter nulls all signals except for quaternary carbons, the DEPT-135 nulls exclusively quaternary carbons. The combination of the two spectra is therefore very useful in spotting non quaternary carbons in the JMSE "quat-only" spectrum. When referring to the presence or absence of quaternary carbon atoms throughout this specification, however, we mean that the given amount or absence of the quaternary carbon is as measured by the quat only JSME NMR method. If one optionally desires to confirm the results, then also using the DEPT135 technique to confirm the presence and amount of a quaternary carbon may be used.

The BPAC used in the present invention and processes to prepare such BPAC have been described in U.S. Pat. No. 5,849,960, which is hereby incorporated by reference in its entirely.

The BPAC of the invention contains an average chain length per molecule ranging from 8-28 carbon atoms. For many surfactant applications the alcohol composition contains an average carbon chain length of 11, 12, 13, 14, 15, 16, 17, 18, 19, 20 or 21 carbon atoms, or any decimal in between, expressed as an average within the range of 11 to 21 carbon atoms. The number of carbon atoms includes carbon atoms along the chain backbone as well as branching carbons.

Preferably, at least 75 wt %, more preferably, at least 90 wt. % of the molecules in the BPAC have chain lengths ranging from 11 to 21, yet more preferably from 14 to 18 carbon atoms. As one feature of the invention, the average number of branches is at least 0.7, as defined and determined above. The compositions having an average number of branches of at least 1.5, in particular ranging from 1.5 to about 2.3, especially from 1.7 to 2.1 are preferred.

A feature of the invention lies in the provision of a BPAC as defined above, having less than 0.5 atom % of Cq's as measured by a quat only JMSE modified 13C-NMR having a detection limit of 0.3 atom % or better, and preferably an BPAC which contains no Cq's as measured by this NMR technique.

In a preferred embodiment of the invention, less than 5%, or more preferably less than 3%, of the alcohol molecules in the BPAC are linear alcohols. The percentage of molecules which are linear may be determined by gas chromatography.

When the branching has been achieved by skeletal isomerization, the BPAC of the invention may be characterized by the NMR technique as having from 5 to 25% branching on the C2 carbon position, relative to the hydroxyl carbon atom. In a more preferred embodiment, from 10 to 20% of the number of branches are at the C2 position, as determined by the NMR technique. The BPAC also generally has from 10% to 50% of the number of branches on the C3 position, more typically from 15% to 30% on the C3 position, also as determined by the NMR technique. When coupled with the number of branches seen at the C2 position, the BPAC in this case contain significant amount of branching at the C2 and C3 carbon positions.

Not only does the BPAC of the invention have a significant number of branches at the C2 and C3 positions, the BPACs may have at least 5%, preferably at least 10, more preferably in the range of from 10 to 20% of isopropyl terminal type of branching, meaning methyl branches at the second to last carbon position in the backbone relative to the hydroxyl carbon. In typical hydroformylated olefins of the NEODOL® series, less than 1%, and usually 0.0%, of the branches are terminal isopropyl branches.

Considering the combined number of branches occurring at the C2, C3, and isopropyl positions, there are embodiments of the invention where at least 20%, more preferably at least 30%, of the branches are concentrated at these positions. The scope of the invention, however, includes branching occurring across the length of the carbon backbone. In another preferred embodiment of the invention, the total number of methyl branches number at least 40%, even at least 50%, of the total number of branches, as measured by the NMR technique described above. This percentage includes the overall number of methyl branches seen by the NMR technique described above within the C1 to the C3 carbon positions relative to the hydroxyl group, and the terminal isopropyl type of methyl branches.

The BPAC may also comprise ethyl branches. The number of ethyl branches can range from 5% to 30%, most typically from 10% to 20%, based on the overall types of branching that the NMR method detects.

The invention also pertains to the use of derivatives of the BPAC. Such derivatives include or alkoxylated alcohols and derived anionic surfactant composition such as alcohol (alkoxy) sulfates, sulfonates, carboxylates, phosphates, alcohol (alkoxy) derivatives having similar head groups.

The BPAC of the invention is suitable for the manufacture of anionic, nonionic, and cationic surfactants, preferably the former two, more preferably the anionic. Specifically, the BPAC of the invention can be used as the pecursor for the manufacture of anionic sulfates, including alcohol sulfates and oxylakylated alcohol sulfates, and nonionic alkoxylated alcohols.

Any technique known for sulfating alcohols can be used herein. The BPAC may be directly sulfated, or first alkoxylated followed by sulfatation. A preferred class of compositions comprises at least one anionic surfactant comprising the condensation product of the C8 to C36, particularly the C11 to C19 BPAC with or without ethylene oxide and/or propylene oxide, in which the number of ethoxy groups ranges from 3 to 12 and the ratio ethoxy/propoxy is from 4 to 12, followed by sulfation.

The general class of anionic surfactants or alcohol ethoxysulfates can be characterized by the chemical formula:

R'—O—(CH2-CH2-O)x-SO3M(II)

wherein R' represents the branched olefin hydrophobe moiety, x represents the average number of oxyethylene groups per molecule and is in the range of from 0 to 12, and M is a cation selected from an alkali metal ion, an ammonium ion, and mixtures thereof. Of course, the surfactant can by alkoxylated with any oxirane containing compound other than, in mixture with, or sequentially with ethylene oxide.

Sulfonation processes are described, for instance, in U.S. Pat. No. 3,462,525, issued Aug. 19, 1969 to Levinsky et al., U.S. Pat. No. 3,428,654 issued Feb. 18, 1969 to Rubinfeld et al., U.S. Pat. No. 3,420,875 issued Jan. 7, 1969 to DiSalvo et al., U.S. Pat. No. 3,506,580 issued Apr. 14, 1970 to Rubinfeld et al., U.S. Pat. No. 3,579,537 issued May 18, 1971 to Rubinfeld et al., and U.S. Pat. No. 3,524,864 issued Aug. 18, 1970 to Rubinfeld. Suitable sulfation procedures include sulphur trioxide (SO3) sulfation, chlorosulfonic acid (ClSO3H) sulfation and sulfamic acid (NH2SO3H) sulfation. When concentrated sulfuric acid is used to sulfate alcohols, the concentrated sulfuric acid is typically from 75 to 100, preferably from 85 to 98 percent by weight, in water. Suitable amounts of sulfuric acid are generally in the range of from 0.3 to 1.3, preferably from 0.4 to 1.0 mole of sulfuric acid per mole of alcohol.

A typical sulphur trioxide sulfation procedure includes contacting liquid alcohol or its ethoxylate and gaseous sulphur trioxide at about atmospheric pressure in the reaction zone of a falling film sulfator cooled by water at a temperature in the range of from 25° C. to 70° C. to yield the sulfuric acid ester of alcohol or its ethoxylate. The sulfuric acid ester of the alcohol or its ethoxylate then exits the falling film column and is neutralized with an alkali metal solution, e.g., sodium or potassium hydroxide, to form the alcohol sulfate salt or the alcohol ethoxysulfate salt.

Suitable alkoxylated alcohols can be prepared by adding to the alcohol or mixture of alcohols to be alkoxylated a calculated amount, e.g., from 0.1 to 0.6, preferably from 0.1 to 0.4 percent by weight, based on total alcohol, of a strong base, typically an alkali metal or alkaline earth metal hydroxide such as sodium hydroxide or potassium hydroxide, which serves as a catalyst for alkoxylation. The resulting mixture is dried, as by vapour phase removal of any water present, and an amount of alkylene oxide calculated to provide from about 1 mole to about 12 moles of alkylene oxide per mole of alcohol is then introduced and the resulting mixture is allowed to react until the alkylene oxide is consumed, the course of the reaction being followed by the decrease in reaction pressure.

The alkoxylation is typically conducted at elevated temperatures and pressures. Suitable reaction temperatures range from 120° C. to 220° C. with the range of from 140° C. to 160° C. being preferred. A suitable reaction pressure is achieved by introducing to the reaction vessel the required amount of alkylene oxide which has a high vapour pressure at the desired reaction temperature. For consideration of process safety, the partial pressure of the alkylene oxide reactant is preferably limited, for instance, to less than 512 kPa, and/or the reactant is preferably diluted with an inert gas such as nitrogen, for instance, to a vapour phase concentration of about 50 percent or less. The reaction can, however, be safely accomplished at greater alkylene oxide concentration, greater total pressure and greater partial pressure of alkyelene oxide if suitable precautions, known to the art, are taken to manage the risks of explosion. With respect to ethylene oxide, a total pressure of between about 376 and 858 kPa, with an ethylene oxide partial pressure between 345 and 621 kPa, is particularly preferred, while a total pressure of between about 50 and 90 psig, with an ethylene oxide partial pressure between 238 and 445 kPa, is considered more preferred. The pressure serves as a measure of the degree of the reaction and the reaction is considered to be substantially complete when the pressure no longer decreases with time.

It should be understood that the alkoxylation procedure serves to introduce a desired average number of alkylene oxide units per mole of alcohol alkoxylate. For example, treatment of an alcohol mixture with 3 moles of ethylene oxide per mole of alcohol serves to effect the ethoxylation of each alcohol molecule with an average of 3 ethylene oxide moieties per mole alcohol moiety, although a substantial proportion of alcohol moieties will become combined with more than 3 ethylene oxide moieties and an approximately equal proportion will have become combined with less than 3. In a typical ethoxylation product mixture, there is also a minor proportion of unreacted alcohol.

Other alkyene oxides can be used, such a proplyene oxide and butylene oxide. These may be added as a heteric mixture to the alcohol or sequentially to make a block stucture.

We claim:

1. A fuel composition comprising a pour point depressant, wherein the pour point depressant is an ester prepared by a process for preparing a branched ester, comprising reacting a branched primary alcohol composition, having from 8 to 28 carbon atoms and an average number of branches per molecule of from 0.7 to 3.0, said branching comprising methyl and ethyl branches, with an acid that is a short chain fatty acid comprising an aliphatic group of two to six carbons.

2. The composition of claim 1, wherein the short chain fatty acid is selected from the group consisting of formic acid, acetic acid, propionic acid, isobutyric acid (2-methylpropanoic acid), butyric acid, isovaleric acid (3-methylbutanoic acid) and valeric acid.

3. The composition, of claim 1, wherein the branched primary alcohol composition has an average number of branches per molecule ranges from 1.0 to 3.0.

4. The composition of claim 1, wherein the branched primary alcohol composition has an average number of branches per molecule ranges from 1.5 to 2.3.

5. The composition of claim 1, wherein the branched primary alcohol composition comprises less than 0.5 atom % of quaternary carbon atoms.

6. The composition of claim 1, wherein the branched primary alcohol composition contains less than 5% of linear alcohols.

7. The composition of claim 1, wherein at least 40% of the number of branches in the branched primary alcohol composition are methyl branches.

8. The composition of claim 1, wherein from 5% to 30% of the number of branches in the branched primary alcohol composition are ethyl branches.

9. The composition of claim 1 wherein the fuel composition is a diesel fuel composition.

* * * * *